United States Patent [19]

Guzik et al.

[11] Patent Number: 5,298,646
[45] Date of Patent: Mar. 29, 1994

[54] SYNTHESIS OF MONOCHLOROETHYL CHLOROFORMATES BY FREE RADICAL INITIATED CHLORINATION OF ETHYL CHLOROFORMATE

[75] Inventors: Frederick F. Guzik, Export; James A. Manner, Monroeville; Suresh B. Damle, Pittsburgh, all of Pa.

[73] Assignee: PPG Industries, Inc., Pittsburgh, Pa.

[21] Appl. No.: 96,326

[22] Filed: Jul. 22, 1993

[51] Int. Cl.$^5$ .............................................. C07C 69/96
[52] U.S. Cl. ..................................... 558/283; 560/226; 560/229
[58] Field of Search ................. 558/283; 560/226, 229

[56] References Cited

U.S. PATENT DOCUMENTS

| | | | |
|---|---|---|---|
| 3,823,175 | 7/1974 | Exner et al. | 558/283 |
| 3,966,786 | 6/1976 | Rozsa et al. | 558/283 |
| 4,592,872 | 6/1986 | Cagnon et al. | 558/283 |
| 4,602,105 | 7/1986 | Drent | 560/229 |

FOREIGN PATENT DOCUMENTS

| | | | |
|---|---|---|---|
| 3135947 | 3/1983 | Fed. Rep. of Germany | 560/226 |
| 2510989 | 2/1983 | France | 560/226 |
| 2592377 | 7/1987 | France | 558/283 |
| 4843489 | 12/1970 | Japan | 560/226 |

Primary Examiner—José G. Dees
Assistant Examiner—Keith MacMillan
Attorney, Agent, or Firm—George D. Morris

[57] ABSTRACT

Ethyl chloroformate is chlorinated in the rectifying zone of a distillation reactor to produce 1-chloroethyl chloroformate and 2-chloroethyl chloroformate.

28 Claims, No Drawings

SYNTHESIS OF MONOCHLOROETHYL CHLOROFORMATES BY FREE RADICAL INITIATED CHLORINATION OF ETHYL CHLOROFORMATE

BACKGROUND OF THE INVENTION

1-Chloroethyl chloroformate [CAS 50893-53-3] and 2-chloroethyl chloroformate [CAS 627-11-2] are known compounds which are useful as intermediates for the synthesis of pharmaceuticals and herbicides. Although these compounds can be produced by the chlorination of ethyl chloroformate [CAS 541-41-3] in the liquid phase or in the vapor phase, the reaction products are heavily contaminated with one or more dichloroethyl chloroformates as by-products. The formation of higher chlorinated by-products is undesirable since the by-products are of lesser value economically and since they often result in disposal problems.

THE INVENTION

A method has now been discovered in which 1-chloroethyl chloroformate and 2-chloroethyl chloroformate may be concurrently produced with improved selectivity by the chlorination of ethyl chloroformate.

Accordingly, in the method wherein ethyl chloroformate is chlorinated in a chlorination system to produce 1-chloroethyl chloroformate and 2-chloroethyl chloroformate, the invention is the improvement wherein: (a) the chlorination system comprises a rectifying zone and a stripping zone, (b) molecular chlorine is introduced to the top of the stripping zone, (c) ethyl chloroformate is countercurrently contacted in the rectifying zone with molecular chlorine, (d) overhead vapor from the rectifying zone is partially condensed to provide a liquid phase comprising liquid ethyl chloroformate and a gaseous phase comprising hydrogen chloride, (e) substantially all of the liquid phase is introduced as reflux to the rectifying zone, (f) the gaseous phase is removed from the chlorination system, (g) bottoms liquid from the stripping zone is boiled to provide reboiled vapors, and (h) liquid from the rectifying zone is countercurrently contacted in the stripping zone with the reboiled vapors.

As used herein, "conversion" is the percentage of ethyl chloroformate converted to other compounds during the reaction, "selectivity" is the ratio of the moles of 1-chloroethyl chloroformate and 2-chloroethyl chloroformate produced to the moles of the ethyl chloroformate converted to all products of the reaction, expressed as percent, and "yield" is the product of "conversion" and "selectivity" divided by one hundred.

Although it is not desired to be bound by any theory, it is believed that the improvement in selectivity is likely due to conducting the chlorination reaction under conditions where the 1-chloroethyl chloroformate and 2-chloroethyl chloroformate, once formed, are quickly removed from the region of chlorination. The normal boiling points of chloroformates having the empirical formula $C_2H_{5-x}Cl_xOC(O)Cl$ where x is 0, 1, or 2, increase with increasing values of x. Examples include ethyl chloroformate (b.p. 93° C.), 1-chloroethyl chloroformate (b.p. 118° C.), 2-chloroethyl chloroformate (b.p. 155° C.), 1,2-dichloroethyl chloroformate (b.p. 159° C.), and 2,2-dichloroethyl chloroformate (b.p. ca. 165° C., estimated). The chlorination may therefore be conducted in a distillation environment where descending liquid is countercurrently contacted in the rectifying zone with molecular chlorine introduced to the system at the top of the stripping zone (and optionally at one or more locations in the rectifying zone) and with vapor ascending from the stripping zone. The normal boiling point of molecular chlorine is much lower than those of the organic materials present in the column. This, together with the temperature gradient existing lengthwise through the column in accordance with the known principles of distillation, causes the molecular chlorine to ascend into the rectifying zone where it can react with ethyl chloroformate and to leave all but the very uppermost portion of the stripping zone substantially free of molecular chlorine. Since the boiling points of the 1-chloroethyl chloroformate and 2-chloroethyl chloroformate are higher than that of the ethyl chloroformate, the 1-chloroethyl chloroformate and 2-chloroethyl chloroformate are encouraged by the temperature gradient to rapidly descend from the rectifying zone into the interior of the stripping zone where conditions do not favor further chlorination. The invention accordingly promotes selectivity by providing conditions which discourage chlorination of the desired products to higher levels of chlorination.

The particular form of apparatus used in practicing the invention may vary widely. Usually, but not necessarily, the rectifying zone and the stripping zone are contained in the same distillation column in which vapor from the top of the stripping zone is allowed to pass upward into the rectifying zone and liquid from the bottom of the rectifying zone is allowed to pass downward into the top of the stripping zone. Examples of various columns that may be used include bubble cap columns, sieve plate columns, packed columns, and similar devices. In all cases the lowest chlorine feed point is considered to be a part of the stripping zone.

The chlorination can be conducted semi-batchwise, continuously, or semi-continuously.

The amount of molecular chlorine introduced to the reactor may vary widely. Factors to be considered include the degree of chlorination of the ethyl chloroformate to be achieved and the identities and amounts of other materials present in the feedstock. In general, sufficient molecular chlorine should be introduced to the chlorination system to accomplish the desired degree of chlorination of the ethyl chloroformate. The ratio of the moles of molecular chlorine introduced to the chlorination system to the moles of ethyl chloroformate introduced to the chlorination system is usually, but not necessarily, in the range of from 0.1:1 to 1.5:1. Often the ratio is in the range of from 0.4:1 to 1:1. From 0.5:1 to 0.9:1 is preferred.

The chlorination is usually, but not necessarily, conducted in the presence of free radical initiator.

The free radical initiators that can be used are numerous and widely varied. In most cases, organic free radical initiators are used.

One class of suitable organic free radical initiators comprises the organic peroxygen-containing free radical initiators. This class may be divided into a large number of subclasses, some of which are as follows:

Peroxides, exemplified by diethyl peroxide, di-tert-butyl peroxide [CAS 110-05-4], n-butyl 4,4-bis(tert-butylperoxy)valerate, 1,1-bis(tert-butylperoxy)-3,3,5-trimethylcyclohexane, bis-tert-butyl peroxides of diisopropylbenzene, dicumyl peroxide [CAS-80-43-3], 2,5-dimethyl-2,5-bis(tert-butylperoxy)hexane [CAS 78-63-7], and 2,5-dimethyl-2,5-bis(tert-butylperoxy)-3-hexyne [CAS 1068-27-5].

Hydroperoxides exemplified by methyl hydroperoxide, tert-butyl hydroperoxide [CAS 75-91-2], cumyl hydroperoxide [CAS 80-15-9], 2,5-dimethyl-2,5-dihydroperoxyhexane [CAS 3025-88-5], p-menthanehydroperoxide [CAS 80-47-7], and diisopropylbenzene hydroperoxide [CAS 98-49-7].

Ketone peroxides, exemplified by methyl ethyl ketone peroxide, methyl isobutyl ketone peroxide, cyclohexanone peroxide, 2,4-pentanedione peroxide, the 1,2,4,5-tetraoxacyclohexanes, and the 1,2,4,5,7,8-hexaoxacyclononanes.

Aldehyde peroxides, exemplified by bis(1-hydroxyheptyl) peroxide.

Diperoxyketals, exemplified by 2,2-bis(tert-butylperoxy)butane [CAS 2167-23-9], ethyl 3,3-bis(tert-butylperoxy)butyrate [CAS 55794-20-2], 1,1-bis(tert-butylperoxy)cyclohexane [CAS 3006-86-8], and 1,1-bis(tert-butylperoxy)-3,3,5-trimethylcyclohexane [CAS 6731-36-8].

Diacyl peroxides, exemplified by diacetyl peroxide [CAS 110-22-5], dibenzoyl peroxide [CAS 94-36-0], dicaprylyl peroxide, bis(4-chlorobenzoyl) peroxide, didecanoyl peroxide, bis(2,4-dichlorobenzoyl) peroxide [CAS 133-14-2], diisobutyryl peroxide [CAS 3437-84-1], diisononanoyl peroxide, dilauroyl peroxide [CAS 105-74-8], dipelargonyl peroxide, dipropionyl peroxide, and bis(3-carboxylpropionyl) peroxide.

Peroxycarboxylic acids, exemplified by peroxyacetic acid.

Peroxyesters, exemplified by tert-butyl peroxyacetate [CAS 107-71-1], methyl peroxyacetate, tert-butyl peroxybenzoate [CAS 614-45-9] tert-butyl peroxy(2-ethylhexanonate) [CAS 3006-82-4], tert-butyl peroxyisobutyrate, tert-butyl peroxypivalate, 2,5-dimethyl-2,5-bis(benzoylperoxy)hexane [CAS 618-77-1], tert-butyl peroxy(2-ethylbutyrate), 2,5-dimethyl-2,5-bis(2-ethylhexanoylperoxy)hexane [CAS 13052-09-0], di-tert-butyl diperoxyazelate [CAS 16580-06-6], tert-amyl peroxy(2-ethylhexanoate) [CAS 686-31-7], di-tert-butyldiperoxyphthalate, 0,0-tert-butyl hydrogen monoperoxymaleate, dimethyl peroxyoxalate, di-tert-butyl diperoxyoxalate, and tert-butyl peroxyneodecanoate [CAS 748-41-4].

Peroxycarbonates, exemplified by tert-butylperoxy isopropyl carbonate.

Peroxydicarbonates, exemplified by diisopropyl peroxydicarbonate [CAS 105-64-6], di-sec-butyl peroxydicarbonate, di-n-propyl peroxydicarbonate [CAS 16066-38-9], di(2-ethylhexyl) peroxydicarbonate, dicyclohexyl peroxydicarbonate [CAS 1561-49-5], and dicetyl peroxydicarbonate [CAS 26322-14-5].

Another class of suitable organic free radical initiators comprises the organic azo-nitrile initiators, of which there are many. Examples of suitable azo-nitrile initiators include 2,2'-azobis(2-methylpropanenitrile) [CAS 78-67-1], 2,2'-azobis(2-methylbutanenitrile) [CAS 13472-08-7], 2,2'-azobis(2,4-dimethylpentanenitrile) [CAS 4419-11-8], 2,2'-azobis(4-methoxy-2,4-dimethylpentanenitrile) [CAS 15545-97-8], 1,1'-azobis(cyclohexanecarbonitrile) [CAS 2094-98-6], 4,4'-azobis(4-cyanopentanoic acid) [CAS 2638-94-0], 2,2'-azobis(2-methylpentanenitrile), 2,2'-azobis(2,3-dimethylbutanenitrile), 2,2'-azobis(2-methylhexanenitrile), 2,2'-azobis(2,3-dimethylpentanenitrile), 2,2'-azobis(2,3,3-trimethylbutanenitrile), 2,2'-azobis(2,4,4-trimethylpentanenitrile), 2,2'-azobis(2-methyl-3-phenylpropanenitrile), 2,2'-azobis(2-cyclohexylpropanenitrile), 1,1'-azobis(cycloheptanecarbonitrile), 1,1'-azobis(cyclooctanecarbonitrile), 1,1'-azobis(cyclodecanecarbonitrile), 2-(tert-butylazo)-4-methoxy-2,4-dimethylpentanenitrile [CAS 55912-17-9], 2-(tert-butylazo)-2,4-dimethylpentanenitrile [CAS 55912-18-0], 2-(tert-butylazo)-2-methylpropanenitrile [CAS 25149-46-6], 2-(tert-butylazo)-2-methylbutanenitrile [CAS 52235-20-8], 1-(tert-amylazo)cyclohexanecarbonitrile [CAS 55912-19-1], 1-(tert-butylazo)cyclohexanecarbonitrile [CAS 25149-47-7], and 2-[(1-chloro-1-phenylethyl)azo]-2-phenylpropanenitrile.

It is believed that many inorganic free radical initiators and metallic organic free radical initiators are suitable for use in the present invention. Examples of inorganic free radical initiators include sodium peroxide [CAS 1313-60-6], lithium peroxide [CAS 12031-80-0], potassium peroxide [CAS 17014-71-0], magnesium peroxide [CAS 14452-57-4], calcium peroxide [CAS 1305-79-9], strontium peroxide [CAS 1314-18-7], barium peroxide [CAS 1304-29-6], the sodium peroxyborates, sodium carbonate sesqui(peroxyhydrate) [CAS 15630-89-4], disodium peroxydicarbonate [CAS 3313-92-6], dipotassium peroxydicarbonate [CAS 589-97-9], monosodium peroxymonocarbonate [CAS 20745-24-8], monopotassium peroxymonocarbonate [CAS 19024-61-4], peroxymonophosphoric acid [CAS 13598-52-2], peroxydiphosphoric acid [CAS 13825-81-5], tetrapotassium peroxydiphosphate [CAS 15593-49-4], tetrasodium pyrophosphate bis[peroxyhydrate] [CAS 15039-07-3], peroxymonosulfuric acid [CAS 7722-86-3], oxone peroxymonosulfate [CAS 37222-66-5], peroxydisulfuric acid [CAS 13445-49-3], diammonium peroxydisulfate [CAS 7727-54-0], dipotassium peroxydisulfate [CAS 7727-21-1], disodium peroxydisulfate [CAS 7775-27-1], and zinc peroxide [CAS 1314-22-3]. Examples of metallic organic free radical initiators include diethyloxyaluminum tert-cumyl peroxide [CAS 34914-67-5], tri-tert-butyl perborate [CAS 22632-09-3], tert-butyl triethylgermanium peroxide [CAS 26452-74-4], dioxybis[triethylgermane] [CAS 58468-05-6], (tert-butyldioxy)triethylplumbane [CAS 18954-12-6], 00-tert-butyl dimethyl phosphorperoxoate [CAS 18963-64-9], tetrakis[tert-butyl] peroxysilicate [CAS 10196-46-0], dioxybis[trimethylsilane] [CAS 5796-98-5], (tert-butyldioxy)trimethylsilane [CAS 3965-63-7], dioxybis[triethylstannane] [CAS 4403-63-8], and (tert-butyldioxy)trimethylstannane [CAS 20121-56-6].

Other examples of free radical initiators are given in *Kirk-Othmer Encyclopedia of Chemical Technology*, third edition, volume 17, pages 1-90 (1982).

The above listing of free radical initiators is illustrative only and not exhaustive; other free radical initiators may be used.

The amount of free radical initiator present in the organic liquid reaction mixture in the rectifying zone during the reaction is susceptible to very wide variation. The amount of free radical initiator introduced depends upon many factors including, but not limited to: the identity and activity of the initiator; the composition of the organic liquid in the rectifying zone; the presence, identities, and concentrations, if any, of free radical poisons or inhibitors; the manner in which the desired initiator concentration is maintained in the rectifying zone; and the solubility of the initiator in the organic liquid present in the rectifying zone. In general the free radical initiator should be present in the rectifying zone in at least an initiating amount. Amounts of initiator in excess of that needed to initiate the reaction are usually inconsequential. When initiator is used, the amount of initiator in the rectifying zone is most often in the range of from 10 to 2000 parts of the initiator per million parts of organic liquid in the rectifying zone, by weight. The amount of initiator in the rectifying zone is frequently in the range of from 50 to 1000 parts of initiator per million parts of organic liquid in the rectifying zone, by weight. From 250 to 750 parts of initiator per million parts of organic liquid in the rectifying zone, by weight is preferred. When sparingly soluble initiator is used, the amount employed may vary extremely widely and large excesses may be used.

The pressure at which the method of the invention is conducted may vary widely. It may be subatmospheric, ambient atmospheric, or superatmospheric. In most cases it is at about ambient atmospheric pressure or a somewhat higher. In many cases the pressure is in the range of from −75 to +350 kilopascals, gauge. Often the pressure is in the range of from 0 to +140 kilopascals, gauge. Preferably the pressure is in the range of from 0 to +70 kilopascals, gauge.

The temperatures at which the method of the invention is conducted may vary considerably. In general, there is a temperature gradient longitudinally through the column in accordance with the general principles of distillation. The temperature at any location in the column is the boiling point of the composition at that location under the prevailing pressure. Usually, but not necessarily, the temperatures are in the range of from about 50° C. to about 120° C. From about 90° C. to about 120° C. is preferred.

Hydrogen chloride is removed from the chlorination system, usually as a gas.

Organic reaction product is removed from the chlorination system. In most instances the organic reaction product is removed as a liquid as is preferred, but it may be vaporized and removed as a gas. Some may be removed as a liquid and some may be removed as a gas. When the chlorination is conducted semi-batchwise, the organic reaction product is removed after the chlorination has been terminated. When the chlorination is conducted continuously, organic reaction product is removed continuously. When the chlorination reaction is conducted semi-continuously, organic reaction product is removed periodically.

1-Chloroethyl chloroformate and 2-chloroethyl chloroformate together usually, but not necessarily, constitute at least 20 percent by weight of the organic reaction product removed from the chlorination system. Often these compounds constitute at least 40 percent by weight of the organic reaction product. At least 50 percent is preferred.

The molar ratio of 1-chloroethyl chloroformate to 2-chloroethyl chloroformate in the organic reaction product removed from the chlorination system is similarly susceptible to wide variation. Usually the molar ratio of 1-chloroethyl chloroformate to 2-chloroethyl chloroformate in the organic reaction product removed from the chlorination system is in the range of from 0.5:1 to 2:1. Frequently the molar ratio is in the range of from 1:1 to 1.5:1. From 1.2:1 to 1.4:1 is preferred.

The organic reaction product removed from the chlorination system may be dealt with as desired. In most cases it is forwarded to a purification system where the desired components are recovered as purified product compounds. The purification system usually comprises one distillation column or a train of distillation columns. Distillation may be accomplished at subatmospheric, ambient atmospheric, or superatmospheric pressures. Subatmospheric pressures are preferred. Pressures in the range of from 25 to 28 kilopascals, absolute, are conveniently used. One type of purification system comprises a batch distillation column. In another purification system, the organic reaction product removed from the reactor is forwarded to a first distillation column. An overhead stream chiefly comprising unreacted ethyl chloroformate is removed from or near the top of the first distillation column and is recycled to the reactor. A bottoms stream from the first distillation column comprising 1-chloroethyl chloroformate, 2-chloroethyl chloroformate, and dichlorinated ethyl chloroformate is removed from or near the bottom of the first distillation column and is forwarded to a second distillation column. An overhead stream predominately comprising 1-chloroethyl chloroformate is removed from or near the top of the second column. A bottoms stream comprising 2-chloroethyl chloroformate and dichlorinated ethyl chloroformate is removed from or near the bottom of the second distillation column.

The invention is further described in conjunction with the following examples which are to be considered illustrative rather than limiting, and in which all parts are parts by weight and all percentages are percentages by weight unless otherwise specified.

EXAMPLE 1

A glass distillation column reactor comprised a vacuum-jacketed 5-plate Oldershaw column having an internal diameter of 2.54 centimeters, a vacuum-jacketed 20-plate Oldershaw column having an internal diameter of 2.54 centimeters, and an intervening vacuum-jacketed adapter having a first inlet. A chlorine cylinder resting on a balance was connected to the first inlet via an intervening flow meter. The 5-plate column served as a rectifying section while the adapter and the 20-plate column served as a stripping section. The 5-plate column was topped by a distillation head/Friedrichs condenser assembly (−5° C. coolant) which was vented to a caustic scrubber. The distillation head also comprised an overhead condensate sampling trap and a second inlet between the trap and the top of the 5-plate column. A syringe pump with a 50-milliter syringe was connected to the second inlet. The bottom of the 20-plate column was fitted to a one-liter multi-neck flask equipped with a thermometer, a sampling port with a polytetrafluoroethylene septum, a magnetic stir bar, and a heating mantle which rested on a stir plate.

An initiator solution was formed by dissolving 0.33 gram of 2,2′-azobis(2-methylpropanenitrile) in 61 grams of ethyl chloroformate. The initiator solution was charged to the syringe. The flask was charged with 590 grams of ethyl chloroformate. The flask was then heated to obtain close to maximum reflux without flooding. The syringe pump was set to feed approximately 5 milliliters of the initiator solution per hour. The introduction of molecular chlorine gas through the first inlet at 0.47 gram per minute was then begun. During the reaction the condenser functioned as a total reflux condenser. Twelve hours later chlorine introduction was terminated and the reaction mixture was allowed to cool. The final reaction product weighed 806 grams. Gas chromatographic analysis of the reaction product showed it to contain 18.8 area percent of ethyl chloroformate, 45.4 area percent of 1-chloroethyl chloroformate, 34.7 area percent of 2-chloroethyl chloroformate, and 1.06 area percent of dichlorinated ethyl chloroformate.

EXAMPLE 2

The apparatus and general procedure of Example I were used except that the chlorine feed rate was 0.24 gram per minute and the chlorination introduction was for 15 hours. The final reaction product weighed 751.1 grams. Gas chromatographic analysis of the reaction product showed it to contain 47.9 area percent of ethyl chloroformate, 29.0 area percent of 1-chloroethyl chloroformate, 22.4 area percent of 2-chloroethyl chloroformate, and 0.65 area percent of dichlorinated ethyl chloroformate.

EXAMPLE 3

The apparatus and general procedure of Example I were used except that the chlorination introduction was for 8 hours. The chlorine feed rate was 0.47 gram per minute. The final reaction product weighed 738 grams. Gas chromatographic analysis of the reaction product showed it to contain 42.3 area percent of ethyl chloroformate, 31.1 area percent of 1-chloroethyl chloroformate, 26.1 area percent of 2-chloroethyl chloroformate, and 0.57 area percent of dichlorinated ethyl chloroformate.

EXAMPLE 4 (Comparative)

A 125-milliliter European-style, multi-neck glass reactor was equipped with a power-driven Trubore® glass stirrer having a polytetrafluoroethylene blade, a thermometer, a gas inlet tube, and a Friedrichs water-cooled condenser vented to a caustic scrubber system. A lecture bottle of molecular chlorine was connected to the gas inlet through an in-line flow meter. The lecture bottle was placed on a balance to follow the amount of chlorine added.

The reactor was charged with 108.5 grams of ethyl chloroformate and 0.11 gram of dibenzoyl peroxide. The reaction mixture was warmed to 85° C. using a heating mantle connected to a Therm-O-Watch® controller. Chlorine gas was introduced according to the schedule of Table 1.

TABLE 1

| Time, hours:minutes | Temperature, °C. | Cl$_2$ Added, grams, cumulative | Remarks |
|---|---|---|---|
| 0:00 | 85 | 0 | Cl$_2$ on. |
| 0:03 | 86 | 1.5 | |
| 0:21 | 87 | 9.0 | |
| 0:33 | 87 | 14.5 | |
| 0:55 | 88 | 24.8 | |
| 1:09 | 88 | 31.6 | |
| 1:27 | 88 | 39.0 | |
| 2:00 | 87 | 56.8 | |
| 2:26 | 90 | 71.0 | Cl$_2$ off. |

A nitrogen purge was applied. The final reaction product weighed 134.7 grams. Gas chromatographic analysis of the reaction product showed it to contain 13.2 area percent of ethyl chloroformate, 50.4 area percent of 1-chloroethyl chloroformate, 25.9 area percent of 2-chloroethyl chloroformate, and 10.6 area percent of dichlorinated ethyl chloroformate.

EXAMPLE 5 (Comparative)

A 125-milliliter European-style, multi-neck glass reactor was equipped with a power-driven Trubore® glass stirrer having a polytetrafluoroethylene blade, a thermometer, a gas inlet tube, and a Friedrichs water-cooled condenser vented to a caustic scrubber system. A lecture bottle of molecular chlorine was connected to the gas inlet through an in-line flow meter. The lecture bottle was placed on a balance to follow the amount of chlorine added.

The reactor was charged with 108.5 grams of ethyl chloroformate and 0.11 gram of diisopropyl peroxydicarbonate. The reaction mixture was warmed to 50° C. using a heating mantle connected to a Therm-O-Watch® controller. Chlorine gas was introduced according to the schedule of Table 2.

TABLE 2

| Time, hours:minutes | Temperature, °C. | Cl$_2$ Added, grams, cumulative | Remarks |
|---|---|---|---|
| 0:00 | 50 | 0 | Cl$_2$ on. |
| 0:05 | 70 | 3.2 | |
| 0:10 | 70 | 6.1 | |
| 0:20 | 68 | 10.4 | |
| 0:30 | 66 | 14.7 | |
| 0:35 | 69 | 17.1 | |
| 0:50 | 66 | 24.5 | |
| 1:13 | 65 | 35.0 | |
| 1:48 | 70 | 50.3 | |
| 2:27 | 70 | 71.0 | Cl$_2$ off. |

A nitrogen purge was applied. The final reaction product weighed 134.4 grams. Gas chromatographic analysis of the reaction product showed it to contain 12.8 area percent of ethyl chloroformate, 54.1 area percent of 1-chloroethyl chloroformate, 23.0 area percent of 2-chloroethyl chloroformate, and 10.2 area percent of dichlorinated ethyl chloroformate.

EXAMPLE 6 (Comparative)

A 125-milliliter European-style, multi-neck glass reactor was equipped with a power-driven Trubore® glass stirrer having a polytetrafluoroethylene blade, a thermometer, a gas inlet tube, and a Friedrichs water-cooled condenser vented to a caustic scrubber system. A lecture bottle of molecular chlorine was connected to the gas inlet through an in-line flow meter. The lecture bottle was placed on a balance to follow the amount of chlorine added.

The reactor was charged with 108.5 grams of ethyl chloroformate and 0.11 gram of diisopropyl peroxydicarbonate. The reaction mixture was warmed to 40° C. using a heating mantle connected to a Therm-O-Watch® controller. Chlorine gas was introduced according to the schedule of Table 3.

TABLE 3

| Time, hours:minutes | Temperature, °C. | Cl$_2$ Added, grams, cumulative | Remarks |
|---|---|---|---|
| 0:00 | 40 | 0 | Cl$_2$ on. |
| 0:02 | 48 | 0.5 | |
| 0:07 | 49 | 1.6 | |
| 0:18 | 58 | 4.4 | |
| 0:26 | 51 | 6.2 | |
| 0:32 | 50 | 7.7 | |
| 1:00 | 50 | 14.0 | |
| 1:27 | 50 | 20.1 | |
| 1:37 | 50 | 22.4 | |
| 2:04 | 50 | 31.3 | |
| 2:24 | 51 | 35.5 | |
| 3:42 | 50 | 47.0 | |
| 4:52 | 50 | 71.0 | Cl$_2$ off. |

A nitrogen purge was applied. The final reaction product weighed 132 grams. Gas chromatographic analysis of the reaction product showed it to contain 6.7 area percent of ethyl chloroformate, 58.9 area percent of 1-chloroethyl chloroformate, 21.3 area percent of 2-chloroethyl chloroformate, and 13.1 area percent of dichlorinated ethyl chloroformate.

EXAMPLE 7 (Comparative)

A 500-milliliter European-style, multi-neck glass reactor was equipped with a power-driven Trubore® glass stirrer having a polytetrafluoroethylene blade, a thermometer, a gas inlet tube, and a Friedrichs water-cooled condenser vented to a caustic scrubber system. A lecture bottle of molecular chlorine was connected to the gas inlet through an in-line flow meter. The lecture bottle was placed on a balance to follow the amount of chlorine added.

The reactor was charged with 325.5 grams of ethyl chloroformate and 0.326 gram of 2,2'-azobis(2-methylpropanenitrile). The reaction mixture was warmed to 87° C. using a heating mantle connected to a Therm-O-Watch® controller. Chlorine gas was introduced according to the schedule of Table 4.

TABLE 4

| Time, hours:minutes | Temperature, °C. | Cl$_2$ Added, grams, cumulative | Remarks |
| --- | --- | --- | --- |
| 0:00 | 87 | 0 | Cl$_2$ on. |
| 0:05 | 91 | 4.2 | |
| 0:11 | 90 | 10.1 | |
| 0:18 | 90 | 16.8 | |
| 0:25 | 90 | 23.4 | |
| 0:45 | 90 | 41.3 | |
| 0:50 | 90 | 46.8 | |
| 1:21 | 90 | 68.5 | |
| 2:15 | 90 | 108.0 | |
| 2:57 | 90 | 144.1 | |
| 4:03 | 91 | 183.8 | |
| 4:17 | 92 | 213.0 | Cl$_2$ off. |

A nitrogen purge was applied. The final reaction product weighed 402 grams. Gas chromatographic analysis of the reaction product showed it to contain 9.9 area percent of ethyl chloroformate, 55.6 area percent of 1-chloroethyl chloroformate, 22.6 area percent of 2-chloroethyl chloroformate, and 12.0 area percent of dichlorinated ethyl chloroformate.

Although the present invention has been described with reference to specific details of certain embodiments thereof, it is not intended that such details should be regarded as limitations upon the scope of the invention except insofar as they are included in the accompanying claims.

We claim:

1. In the method wherein ethyl chloroformate is chlorinated in a chlorination system to produce 1-chloroethyl chloroformate and 2-chloroethyl chloroformate, the improvement wherein:
   (a) said chlorination system comprises a rectifying zone and a stripping zone,
   (b) molecular chlorine is introduced to the top of said stripping zone,
   (c) ethyl chloroformate is countercurrently contacted in said rectifying zone with molecular chlorine,
   (d) overhead vapor from said rectifying zone is partially condensed to provide a liquid phase comprising liquid ethyl chloroformate and a gaseous phase comprising hydrogen chloride,
   (e) substantially all of said liquid phase is introduced as reflux to said rectifying zone,
   (f) said gaseous phase is removed from said chlorination system,
   (g) bottoms liquid from said stripping zone is boiled to provide reboiled vapors, and
   (h) liquid from said rectifying zone is countercurrently contacted in said stripping zone with said reboiled vapors.

2. The method of claim 1 wherein the ratio of the moles of said molecular chlorine introduced to said chlorination system to the moles of said ethyl chloroformate introduced to said chlorination system is in the range of from 0.1:1 to 1.5:1.

3. The method of claim 1 wherein the pressure is in the range of from −75 to 350 kilopascals, gauge.

4. The method of claim 1 wherein organic reaction product is removed from said chlorination system.

5. the method of claim 4 wherein the chlorination is conducted semi-batchwise or continuously.

6. The method of claim 4 wherein 1-chloroethyl chloroformate and 2-chloroethyl chloroformate together constitute at least 20 percent by weight of the organic reaction product removed from said chlorination system.

7. The method of claim 4 wherein the molar ratio of 1-chloroethyl chloroformate to 2-chloroethyl chloroformate in the organic reaction product removed from said chlorination system is in the range of from 0.5:1 to 2:1.

8. The method of claim 1 wherein said rectifying zone contains free radical initiator.

9. The method of claim 8 wherein said free radical initiator is organic free radical initiator.

10. The method of claim 8 wherein said free radical initiator is 2,2'-azobis(2-methylpropanenitrile).

11. The method of claim 8 wherein the amount of said initiator in said rectifying zone is in the range of from 10 to 2000 parts of said initiator per million parts of organic liquid in said rectifying zone, by weight.

12. The method of claim 8 wherein the amount of said initiator in said rectifying zone is in the range of from 50 to 1000 parts of said initiator per million parts of organic liquid in said rectifying zone, by weight.

13. The method of claim 8 wherein the amount of said initiator in said rectifying zone is in the range of from 250 to 750 parts of said initiator per million parts of organic liquid in said rectifying zone, by weight.

14. The method of claim 8 wherein the ratio of the moles of said molecular chlorine introduced to said chlorination system to the moles of said ethyl chloroformate introduced to said chlorination system is in the range of from 0.1:1 to 1.5:1.

15. The method of claim 8 wherein the ratio of the moles of said molecular chlorine introduced to said chlorination system to the moles of said ethyl chloroformate introduced to said chlorination system is in the range of from 0.4:1 to 1:1.

16. The method of claim 8 wherein the ratio of the moles of said molecular chlorine introduced to said chlorination system to the moles of said ethyl chloroformate introduced to said chlorination system is in the range of from 0.5:1 to 0.9:1.

17. The method of claim 8 wherein the pressure is in the range of from −75 to +350 kilopascals, gauge.

18. The method of claim 8 wherein the pressure is in the range of from 0 to 140 kilopascals, gauge.

19. The method of claim 8 wherein the pressure is in the range of from 0 to 70 kilopascals, gauge.

20. The method of claim 8 wherein organic reaction product is removed from said chlorination system.

21. the method of claim 20 wherein the chlorination is conducted semi-batchwise or continuously.

22. The method of claim 20 wherein 1-chloroethyl chloroformate and 2-chloroethyl chloroformate together constitute at least 20 percent by weight of the organic reaction product removed from said chlorination system.

23. The method of claim 20 wherein 1-chloroethyl chloroformate and 2-chloroethyl chloroformate together constitute at least 40 percent by weight of the organic reaction product removed from said chlorination system.

24. The method of claim 20 wherein 1-chloroethyl chloroformate and 2-chloroethyl chloroformate together constitute at least 50 percent by weight of the organic reaction product removed from said chlorination system.

25. The method of claim 20 wherein the molar ratio of 1-chloroethyl chloroformate to 2-chloroethyl chloroformate in the organic reaction product removed from said chlorination system is in the range of from 0.5:1 to 2:1.

26. The method of claim 20 wherein the molar ratio of 1-chloroethyl chloroformate to 2-chloroethyl chloroformate in the organic reaction product removed from said chlorination system is in the range of from 1:1 to 1.5:1.

27. The method of claim 20 wherein the molar ratio of 1-chloroethyl chloroformate to 2-chloroethyl chloroformate in the organic reaction product removed from said chlorination system is in the range of from 1.2:1 to 1.4:1.

28. The method of claim 27 wherein:
(a) said free radical initiator is 2,2'-azobis(2-methylpropanenitrile);
(b) the amount of said initiator in said rectifying zone is in the range of from 250 to 750 parts of said initiator per million parts of organic liquid in said rectifying zone, by weight;
(c) the ratio of the moles of said molecular chlorine introduced to said chlorination system to the moles of said ethyl chloroformate introduced to said chlorination system is in the range of from 0.5:1 to 0.9:1;
(d) the pressure is in the range of from 0 to 70 kilopascals, gauge;
(e) the chlorination is conducted semi-batchwise or continuously; and
(f) 1-chloroethyl chloroformate and 2-chloroethyl chloroformate together constitute at least 50 percent by weight of the organic reaction product removed from said chlorination system.

* * * * *